United States Patent
Daniel

(10) Patent No.: US 10,182,914 B2
(45) Date of Patent: *Jan. 22, 2019

(54) METHOD OF IMPLANTING A PENILE PROSTHETIC WITH A TOOL HAVING MOVABLE JAWS

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/456,603

(22) Filed: Mar. 13, 2017

(65) Prior Publication Data

US 2017/0181855 A1 Jun. 29, 2017

Related U.S. Application Data

(63) Continuation of application No. 14/499,254, filed on Sep. 29, 2014, now Pat. No. 9,642,707.

(30) Foreign Application Priority Data

Oct. 15, 2014 (EP) .................................... 14188938

(51) Int. Cl.
| | |
|---|---|
| *A61F 5/00* | (2006.01) |
| *A61F 2/26* | (2006.01) |
| *A61F 5/41* | (2006.01) |
| *A61B 17/34* | (2006.01) |
| *A61B 50/30* | (2016.01) |
| *A61F 2/00* | (2006.01) |

(52) U.S. Cl.
CPC ............ *A61F 2/26* (2013.01); *A61B 17/3468* (2013.01); *A61B 50/30* (2016.02); *A61F 2/0095* (2013.01); *A61F 5/41* (2013.01); *A61F 2250/0003* (2013.01)

(58) Field of Classification Search
CPC .................................... A61F 2/26; A61F 5/41
USPC ............... 600/38–41; 606/53–115, 119–128, 606/139–158, 205–211
See application file for complete search history.

(56) References Cited

U.S. PATENT DOCUMENTS

| | | |
|---|---|---|
| 3,704,712 A | 11/1972 | Giesy et al. |
| 3,893,456 A | 7/1975 | Small et al. |
| 4,049,002 A | 9/1977 | Kletschka et al. |
| 4,066,073 A | 1/1978 | Finney et al. |
| 4,201,202 A | 5/1980 | Finney et al. |
| 4,244,370 A | 1/1981 | Furlow et al. |
| 4,342,308 A | 8/1982 | Trick |
| 4,350,151 A | 9/1982 | Scott |

(Continued)

FOREIGN PATENT DOCUMENTS

| | | |
|---|---|---|
| CA | 1142049 A1 | 3/1983 |
| CN | 2737308 Y | 11/2005 |

(Continued)

*Primary Examiner* — John Lacyk
(74) *Attorney, Agent, or Firm* — Coloplast Corp., Coloplast A/S; Nick Baumann

(57) ABSTRACT

A method of implanting a penile prosthetic includes using a tool and grasping a penile prosthesis between a first jaw and a second jaw of the tool. The method includes inserting the first jaw and the second jaw and a portion of the penile prosthesis into the dilated corpora cavernosum, releasing the penile prosthesis from the jaws, and removing the jaws out the dilated corpora.

12 Claims, 9 Drawing Sheets

(56) References Cited

U.S. PATENT DOCUMENTS

| | | | |
|---|---|---|---|
| 4,353,360 A | 10/1982 | Finney et al. | |
| 4,369,771 A | 1/1983 | Trick | |
| 4,399,812 A | 8/1983 | Whitehead | |
| 4,449,520 A | 5/1984 | Palomar et al. | |
| 4,558,693 A | 12/1985 | Lash et al. | |
| 4,653,485 A | 3/1987 | Fishell | |
| 4,726,360 A | 2/1988 | Trick et al. | |
| 4,773,403 A | 9/1988 | Daly | |
| 4,823,779 A | 4/1989 | Daly et al. | |
| 4,829,990 A | 5/1989 | Thüroff et al. | |
| 4,896,678 A | 1/1990 | Ogawa | |
| 4,919,152 A | 4/1990 | Ger | |
| 4,995,380 A | 2/1991 | Maerzke et al. | |
| 5,167,611 A | 12/1992 | Cowan | |
| 5,230,694 A | 7/1993 | Rosenblum | |
| 5,344,388 A | 9/1994 | Maxwell et al. | |
| 5,484,450 A | 1/1996 | Mohamed | |
| 5,788,627 A | 8/1998 | Subrini | |
| 5,828,757 A | 10/1998 | Michalsen et al. | |
| 5,868,729 A | 2/1999 | Pelfrey | |
| 5,895,424 A | 4/1999 | Steele, Sr. et al. | |
| 5,899,849 A | 5/1999 | Elist | |
| 5,968,067 A | 10/1999 | Mooreville et al. | |
| 6,475,244 B2 | 11/2002 | Herweck et al. | |
| 6,579,230 B2 | 6/2003 | Yachia et al. | |
| 6,808,489 B2 | 10/2004 | George et al. | |
| 6,808,490 B1 | 10/2004 | Ling et al. | |
| 7,066,878 B2 | 6/2006 | Eid | |
| 7,344,554 B2 | 3/2008 | Kuyava et al. | |
| 7,407,482 B2 | 8/2008 | Kuyava | |
| 7,914,578 B2 | 3/2011 | Vardi | |
| 7,938,770 B2 | 5/2011 | Morningstar et al. | |
| 7,959,556 B2 | 6/2011 | Morningstar | |
| 8,002,692 B2 | 8/2011 | Morningstar et al. | |
| 8,167,788 B2 | 5/2012 | Fogarty et al. | |
| 8,192,352 B2 | 6/2012 | Morningstar et al. | |
| 8,231,521 B2 | 7/2012 | Morningstar et al. | |
| 8,360,959 B2 | 1/2013 | Morningstar | |
| 8,403,825 B2 | 3/2013 | Morningstar | |
| 8,419,612 B2 | 4/2013 | Daniel | |
| 8,491,621 B2 | 7/2013 | Morningstar | |
| 8,545,391 B2 | 10/2013 | Kuyava et al. | |
| 8,636,645 B2 | 1/2014 | Daniel | |
| 8,685,011 B2 | 4/2014 | Arcand | |
| 8,702,589 B2 | 4/2014 | Kuyava | |
| 9,642,707 B2 * | 5/2017 | Daniel | A61B 17/3468 |
| 2001/0005787 A1 | 6/2001 | Oz et al. | |
| 2006/0225894 A1 | 10/2006 | Roll et al. | |
| 2009/0048537 A1 | 2/2009 | Lydon et al. | |
| 2010/0010530 A1 | 1/2010 | Rhee | |
| 2010/0160722 A1 | 6/2010 | Kuyava et al. | |
| 2011/0066226 A1 | 3/2011 | Bell et al. | |
| 2011/0196271 A1 | 8/2011 | Forsell | |
| 2012/0022323 A1 | 1/2012 | Forsell | |
| 2012/0022324 A1 | 1/2012 | Forsell | |
| 2012/0157763 A1 | 6/2012 | Darnell | |
| 2012/0157764 A1 | 6/2012 | Borgaonkar et al. | |
| 2013/0041212 A1 | 2/2013 | Chechik | |
| 2013/0116655 A1 | 5/2013 | Bacino et al. | |
| 2013/0226131 A1 | 8/2013 | Bacino et al. | |
| 2016/0038167 A1 | 2/2016 | Poucher | |
| 2016/0038288 A1 | 2/2016 | Poucher | |
| 2016/0067045 A1 | 3/2016 | Daniel | |

FOREIGN PATENT DOCUMENTS

| | | |
|---|---|---|
| CN | 201668855 U | 12/2010 |
| CN | 201668856 U | 12/2010 |
| CN | 201988037 U | 9/2011 |
| CN | 203001114 U | 6/2013 |
| DE | 3741879 A1 | 6/1988 |
| DE | 102010038975 A1 | 2/2012 |
| DE | 102010062072 A1 | 5/2012 |
| EP | 0682923 A1 | 11/1995 |
| EP | 0925764 A1 | 6/1999 |
| EP | 2415422 A | 2/2012 |
| ES | 1015196 U | 6/1991 |
| FR | 2532551 A1 | 3/1984 |
| IT | 223594 U | 7/1995 |
| IT | 1296983 B1 | 8/1999 |
| KR | 20050075497 A | 7/2005 |
| KR | 100596497 B1 | 7/2006 |
| KR | 20090122545 A | 12/2009 |
| KR | 100944789 B1 | 2/2010 |
| RU | 35594 U1 | 1/2004 |
| RU | 58341 U1 | 11/2006 |
| SU | 1084016 A1 | 4/1984 |
| WO | 8601398 A1 | 3/1986 |
| WO | 03071970 A1 | 9/2003 |
| WO | 2004045421 A1 | 6/2004 |
| WO | 2005072626 A1 | 8/2005 |
| WO | 2011023197 A1 | 3/2011 |
| WO | 2011035787 A1 | 3/2011 |
| WO | 2011072692 A1 | 6/2011 |
| WO | 12069643 A1 | 5/2012 |
| WO | 2013049682 A1 | 4/2013 |
| WO | 14052729 A2 | 4/2014 |
| WO | 14099873 A1 | 6/2014 |

* cited by examiner

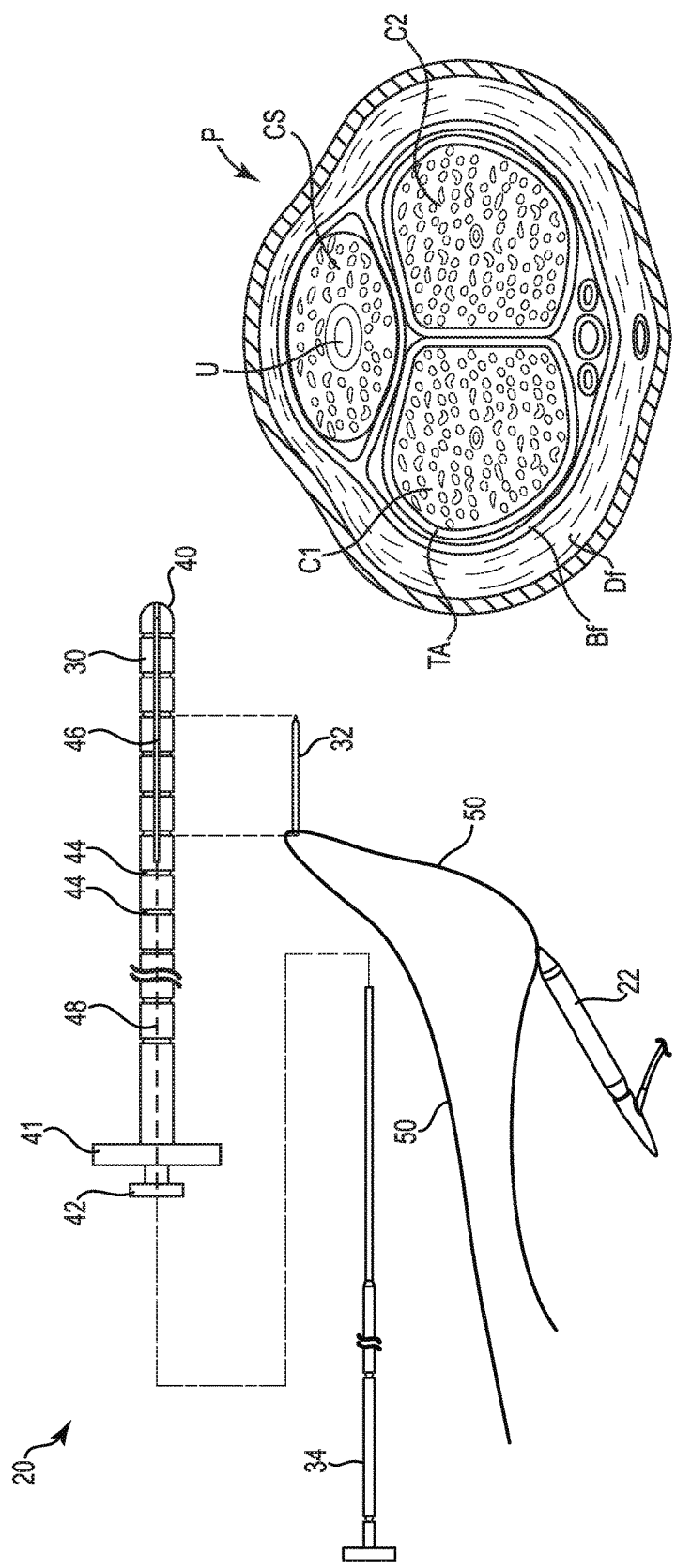

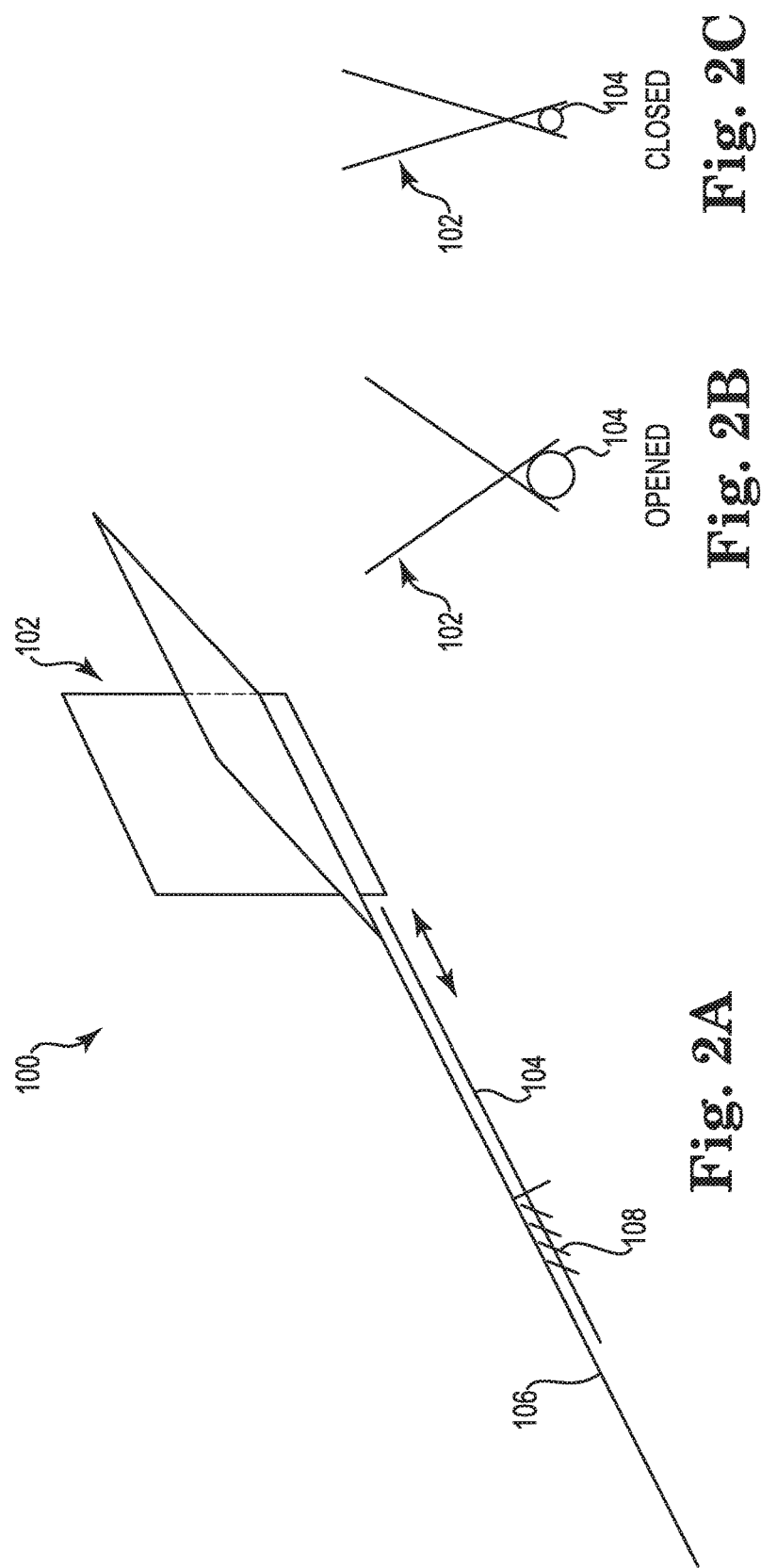

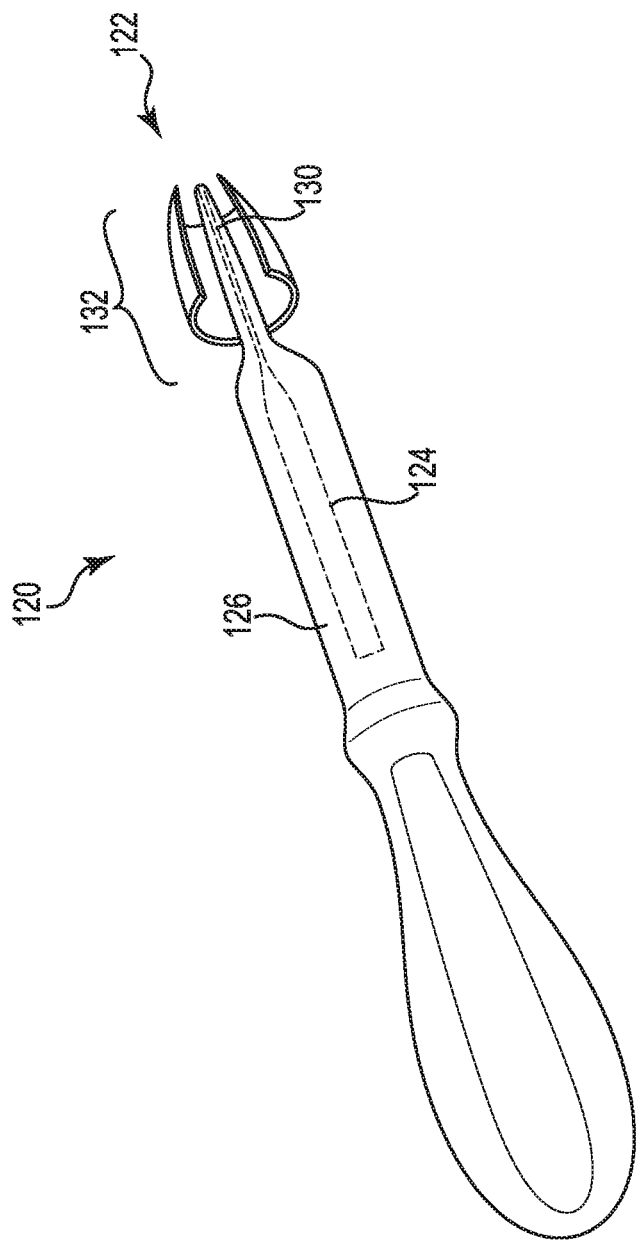

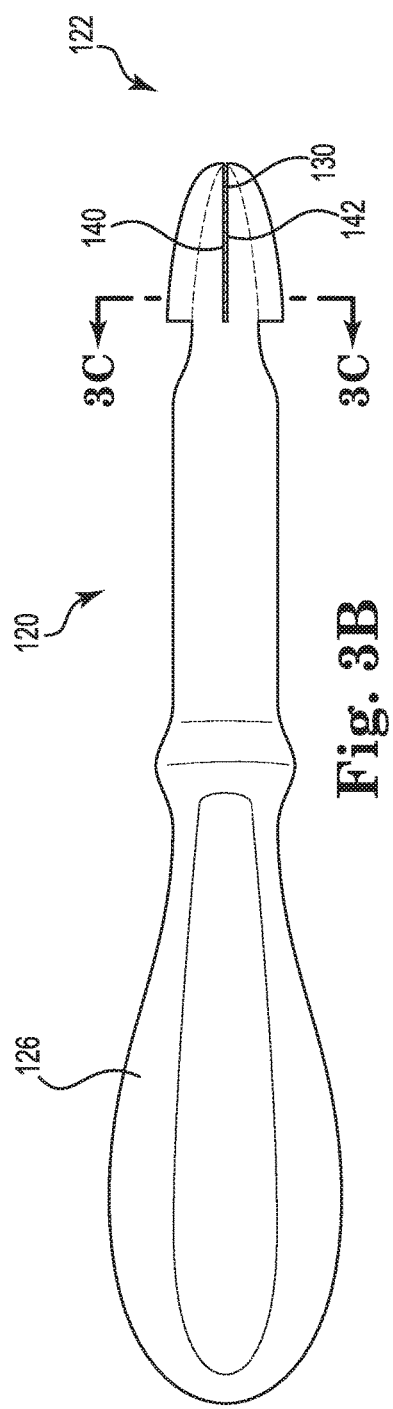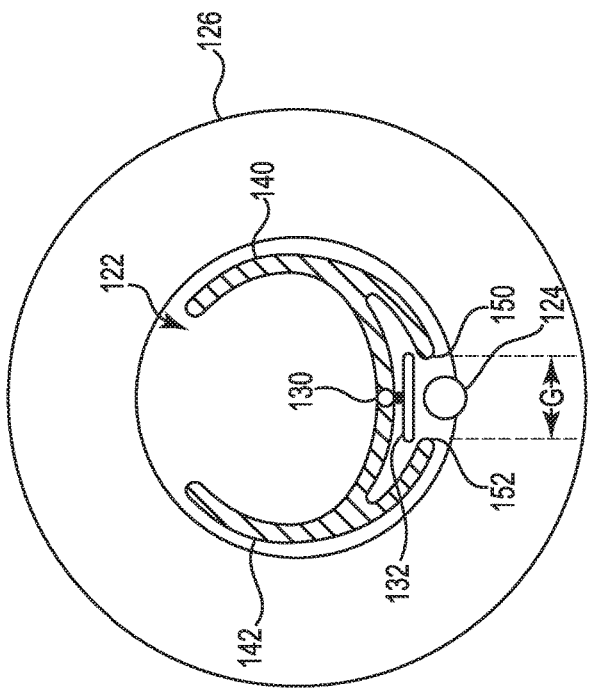
Fig. 3B
Fig. 3C

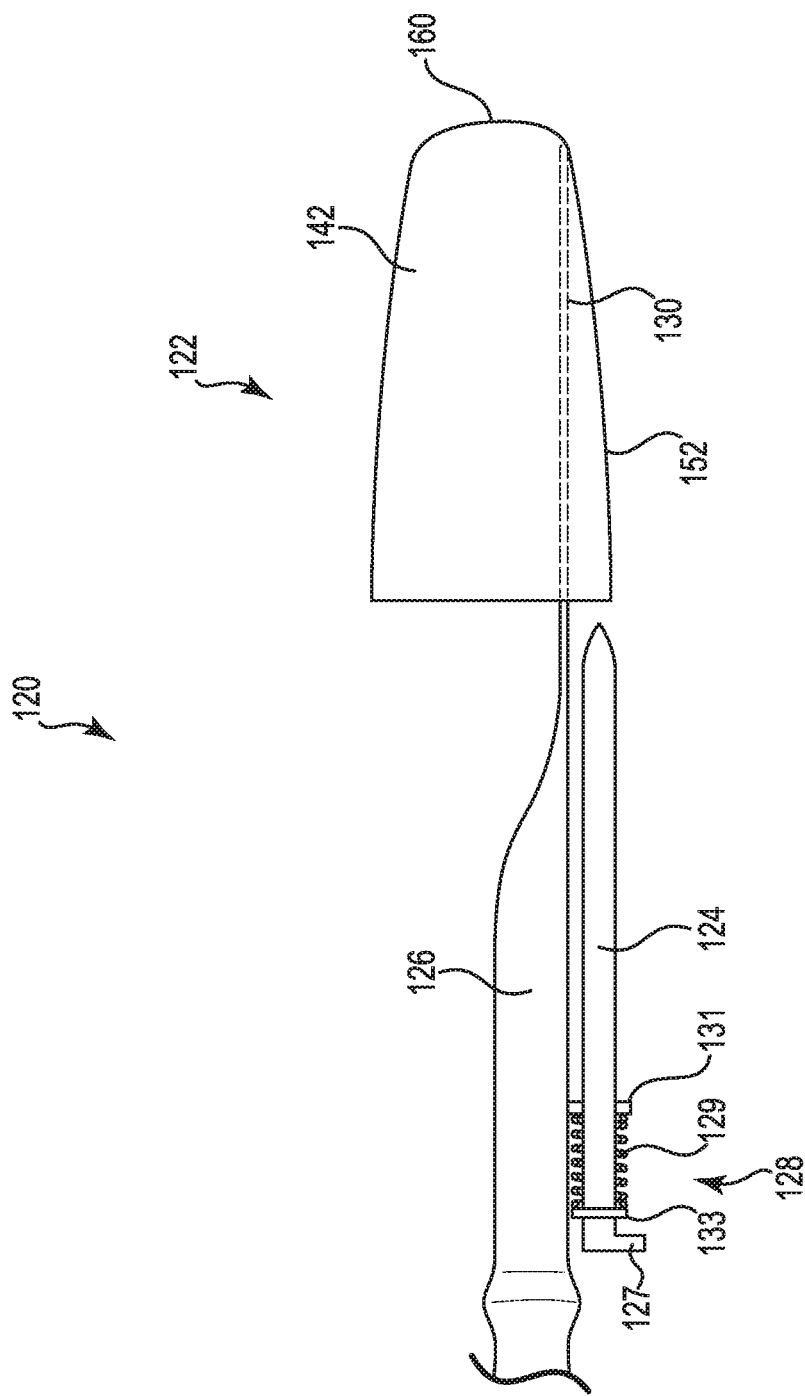

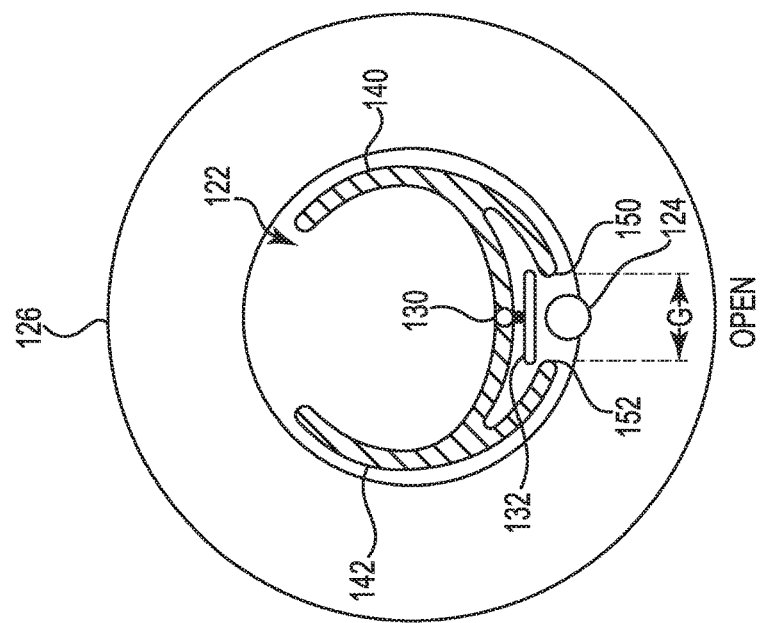
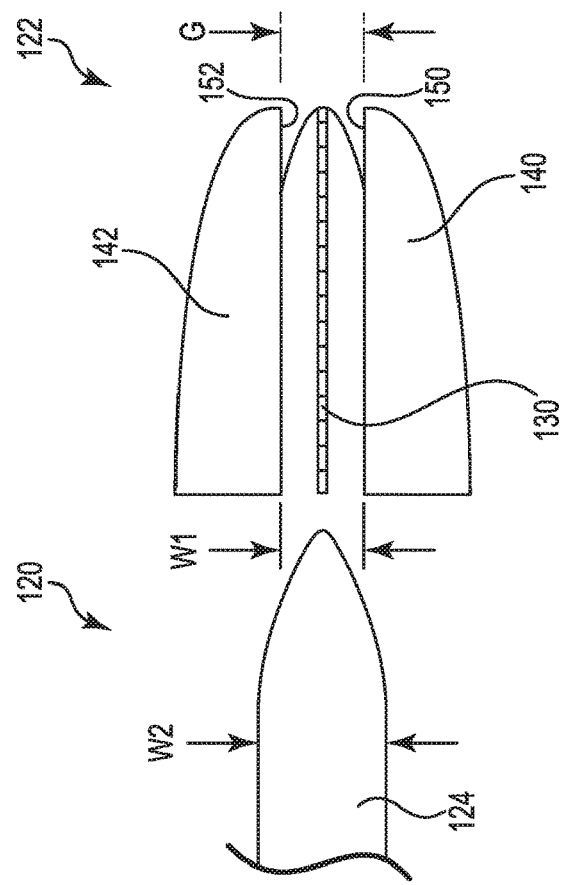

METHOD OF IMPLANTING A PENILE PROSTHETIC WITH A TOOL HAVING MOVABLE JAWS

BACKGROUND

An implanted penile prosthetic has proven useful in treating erectile dysfunction in men. The penile prosthetic includes two inflatable cylinders implanted in the penis, a pump implanted in the scrotum or other internal space, and a liquid holding reservoir implanted in the abdomen or other internal space.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (e.g., a "Furlow" introducer) is inserted into each dilated corpora cavernosum to measure a length of the penis distally and proximally to determine a desired length of the cylinders. A cylinder of the appropriately selected length is secured to a suture, and the suture is secured to a needle (sometimes called a "Keith" needle) that is loaded into the Furlow introducer. The Furlow introducer delivers the needle through the dilated corpora cavernosum and out the glans penis. The needle is discarded and the suture is employed to tow the cylinder into place within the dilated corpora cavernosum.

The above-described procedure has proven effective when implanting penile prostheses. However, surgeons and users would both appreciate improved tools for implanting penile prosthetic cylinders.

SUMMARY

One aspect provides a tool for implanting an inflatable penile prosthetic cylinder. The tool includes a pincher and a plunger coupled to a handle of the tool and movable relative to the pincher. The pincher has a spine portion that is movably coupled to a distal end portion of the handle and a first jaw movably coupled to a second jaw along the spine portion of the pincher. The first jaw has a first plunger edge that is spaced a gap distance away from a second plunger edge of the second jaw. The plunger is tapered having a first width at a distal end that is not greater than the gap distance and a second width that is larger than the first width. The second width measured proximal of the distal end of the plunger.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is an exploded side view of a prior art tool for implanting a cylinder into a penis as illustrated in cross-section in FIG. 1B.

FIG. 2A is a schematic perspective view and FIGS. 2B and 2C are schematic back views of one embodiment of a tool for implanting an inflatable penile cylinder.

FIG. 3A is a perspective view, FIG. 3B is a top view, and FIG. 3C is a cross-sectional view of one embodiment of a tool for implanting an inflatable penile cylinder.

FIG. 4 is a side view of the tool illustrated in FIG. 3A.

FIG. 5A is a bottom view and FIG. 5B is a cross-sectional view of the tool illustrated in FIG. 3A with pinchers in an open position.

DETAILED DESCRIPTION

Figure 6B:
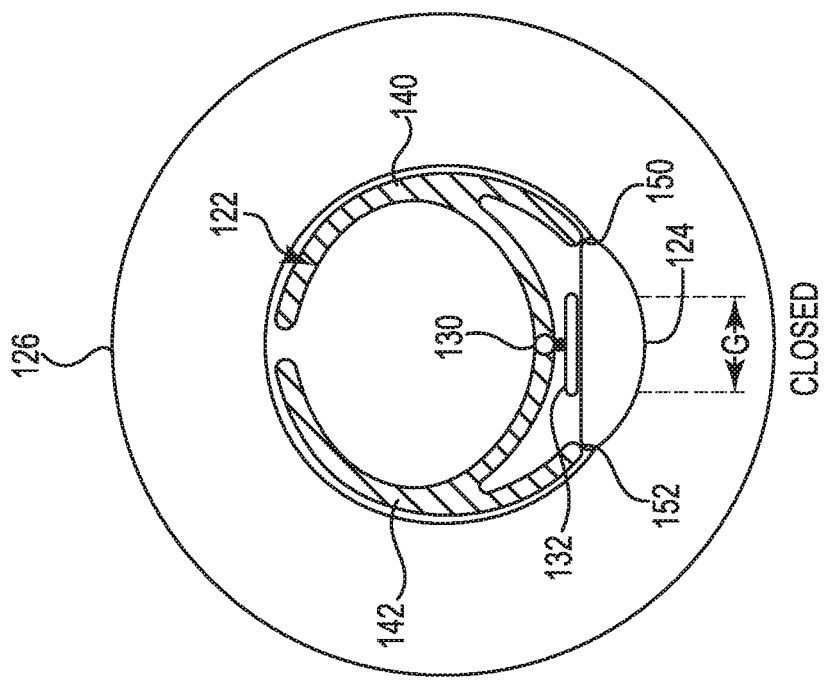
FIG. 6A is a bottom view and FIG. 6B is a cross-sectional view of the tool illustrated in FIG. 3A with the pinchers in a closed position.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

End means endmost. A distal end is the furthest endmost location of a distal portion of a thing being described, whereas a proximal end is the nearest endmost location of a proximal portion of the thing being described. The portion next to or adjacent to an end is an end portion.

An implantable penile prosthetic system includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

FIG. 1A is an exploded side view of a prior art tool 20 for implanting an inflatable cylinder 22 into a penis P illustrated in FIG. 1B. The inflatable cylinders 22 are fabricated to be pliant and comfortable when deflated and rigid and erect when inflated. The deflated cylinder 22 lacks column strength and will bend and twist and resist being pushed into the penis P. For this reason, a suture or strand is employed to pull the inflatable cylinder into place within the penis P.

The tool 20 includes a barrel 30, a needle 32 that is insertable into the barrel 30, and a plunger 34 that is insertable into the barrel 30 to push the needle 32 out of the barrel 30. One such needle 32 is a Keith needle.

The barrel 30 extends between a curved distal end 40 and a handle 41 provided at a proximal end 42. The barrel 30 has markings 44 applied on an external surface to indicate or measure a depth to which the barrel 30 has been inserted into the corpora cavernosum. The barrel 30 is provided with a slot 46 that is sized to receive the needle 32 and a lumen 48 sized to receive the needle 32 and the plunger 34.

The needle 32 is attached to a tow suture 50 that is coupled with the cylinder 22. The tow suture 50 is generally inserted through an eyelet of the needle 50 and a hole provided at a distal end of the cylinder 22.

The plunger 34 is insertable into the lumen 48 at the proximal end 42 of the barrel 30 and operates to push the needle 32 out of the lumen 48.

FIG. 1B is a cross-sectional view of the penis P oriented to access by the surgeon. The surgeon gains access to the corpora cavernosa though small incisions made through the fascia after the penis is reclined toward the abdomen, as illustrated in the cross-sectional view of FIG. 1B. In the view of FIG. 1B the penis P of the patient is reclined against the torso such that the urethra U, surrounded by corpus spongiosum CS tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated with an appropriate dilation tool to form a recess in the penis P that is sized to receive one of the two cylinders 22. The barrel 30 of the tool 20 is inserted into each dilated corpora cavernosum C1, C2 to measure the length of the corpora prior to selecting an appropriately sized cylinder 22. The barrel 30 is removed from the penis P. The suture 50 is inserted through the distal, leading end of the cylinder 22 and the needle 32. The needle 32 is loaded into the barrel 30 through the slot 46 and the plunger 34 is inserted into the lumen 48 via the proximal end 42 of the barrel 30. The barrel 30 is inserted into the dilated corpora cavernosum and the plunger 34 is pushed into the lumen 48 to push the needle 32 out of the barrel 30 and through the glans penis. The surgeon captures the needle 32, disengages the needle 32 from the tow suture 50, and pulls on the tow suture 50 to draw the cylinder 22 into the dilated corpora cavernosum. The tow suture 50 is disengaged from the cylinder, which is now implanted within the corpora cavernosum C1 or C2.

Pushing the needle 32 through the glans penis can cause bleeding from the head of the penis, which while harmless, can be alarming to the patient. Surgeons have expressed a desire to avoid the use of the needle 32.

As noted above, the suture 50 is inserted through the distal, leading end of the cylinder 22. The distal end of the cylinder 22 is oftentimes structurally reinforced to accommodate the hole that the suture 50 is passed through. The reinforced end of the cylinder can be felt by some patients who perceive it as a hard and unnatural, undesirable pointed projection.

Embodiments provide a tool for implanting an inflatable penile prosthetic cylinder into a penis, where the tool does away with the handling and the use of needles, such as a Keith needle. The tool is useful for positively engaging with the cylinder and pushing the prosthetic cylinder into the opening formed in the penis. The tool operates to secure the cylinder in the distal region of the corpora cavernosum with access into and out of the penis through a single incision/opening. The tool may be fabricated from plastic or metal and can be provided in both disposable and reusable forms.

FIG. 2A is a schematic perspective view and FIGS. 2B and 2C are simplified back end views of one embodiment of a tool 100 for implanting an inflatable penile cylinder.

The tool 100 includes a pincher 102 that moves in response to a plunger 104 that is coupled to a handle 106. The plunger 104 is movable in a distal direction toward the pincher 102 and in a proximal direction back toward the handle 106. The plunger 104 is coupled with the handle 106 and includes a bias feature 108 that allows the plunger 104 to return to a neutral position after activating the pincher 102. One suitable bias feature 108 is a coiled spring.

Embodiments of the plunger 104 include a tapered plunger that interacts with the pincher 102 to move the pincher 102 between open and closed positions. For example, the tool 100 operates to grasp an inflatable cylinder within the pincher 102 in response to movement of the plunger 104. The surgeon inserts the cylinder into the pincher 102 and moves the plunger to secure the cylinder within the pincher 102. The pincher 102 and the cylinder is inserted into the dilated corpora. Releasing or activating the plunger 104 releases the grasp of the pincher 102 from the cylinder, allowing the surgeon to remove the tool 100, leaving the cylinder in the corpora. In one embodiment, the plunger 104 is moved in a distal direction to secure the cylinder within the pincher 102. In one embodiment, the plunger 104 is moved in a proximal direction to secure the cylinder within the pincher 102.

Aspects of the disclosed pincher(s) provide the advantageous technical effect of grasping a cylinder in a manner that allows the cylinder to be delivered into a dilated corpora while yet allowing the pincher(s) to release the cylinder and slide out of the corpora and leaving the cylinder in place within the penis.

Aspects of the disclosed plunger(s) provide the advantageous technical effect of closing the pincher to allow the pincher to grasp a cylinder in a manner that allows the cylinder to be delivered into a dilated corpora, and to reversibly open the pincher to allow the pincher(s) to release the cylinder and slide out of the corpora and leaving the cylinder in place within the penis.

FIG. 2B is a back end view of the plunger 104 not in contact with the pincher 102 such that the pincher 102 is in an open position.

FIG. 2C is a back end view illustrating a proximal portion of the plunger 104 in contact with edges of the pincher 102 in a manner that closes the pincher 102.

FIG. 3A is a perspective view of one embodiment of a tool 120 useful for implanting an inflatable penile cylinder. The tool 120 includes a pincher 122 that moves between open enclosed positions in response to movement of a plunger 124 that is coupled with a handle 126. In this view, the plunger 124 is underneath the handle 126.

In one embodiment, the pincher 122 has a spine portion 130 that is movably coupled to a distal end portion 132 of the handle 126. The plunger 124 is coupled to the handle 126 and moves in the distal direction to force the pincher 122 into a closed arrangement.

FIG. 3B is a top view of the tool 120 showing the pincher 122, and FIG. 3C is an end view of the pincher 122. The pincher 122 includes a first jaw 140 that is movably coupled to a second jaw 142 along the spine portion 130 of the pincher 122. The first jaw 140 has a first plunger edge 150 that is spaced a gap distance G away from a second plunger edge 152 of the second job 142. The plunger 124 is located between the first and second jaw edges 150, 152. Movement of the plunger 124 in the distal direction pushes the first plunger edge 150 away from the second plunger edge 152 (thus increasing the gap distance G), which moves at least the superior portion (upper portion) of the first jaw 140 closer to the second jaw 142.

FIG. 4 is a side view of a portion of the tool 120. In one embodiment, the plunger 124 is located under, or inferior, relative to the handle 126 and the second plunger edge 152 is located under, or inferior, relative to the spine portion 130. The plunger 124 is coupled to and movable relative to the handle 126 and includes a push button 127 and a bias feature 128. The push button 127 allows the surgeon to operate or move the plunger 124 and the bias feature 128 returns the plunger 124 to its steady state position. In one embodiment, the bias feature 128 is a coiled spring 129 that is seated between a flange 131 connected to the handle 126 and a separate flange 133 connected to the plunger 124.

In one embodiment, the pincher 122 includes a streamlined bullet-shaped profile that tapers to a rounded distal end 160. In one embodiment, a side view profile of the pincher 122 mimics or is similar to a side view profile of the inflatable cylinder that is implantable into the penis. Other shapes for the pincher 122 are also acceptable.

FIG. 5A is a bottom view and FIG. 5B is an end view of the pincher 122 of the tool 120 in an open position.

The first jaw 140 is coupled to the second jaw 142 along the spine portion 130. The first plunger edge 150 is spaced by the gap distance G away from the second plunger edge 152. In one embodiment, the plunger 124 is tapered and is provided with a first width W1 at a distal end that is not greater than the gap distance G and a second width W2 that is larger than the first width W1. The second width W2 is measured proximal of the distal end of the plunger 124 where the first width W1 is measured. In one embodiment, the first width W1 is less than the gap distance G, and the second width W2 is larger than the first width W1 and larger than the gap distance G. In the open position, the plunger 124 is outside of the edges 150, 152 and is not engaged to move the jaws 140, 142 of the pincher 122.

Figure 6A:
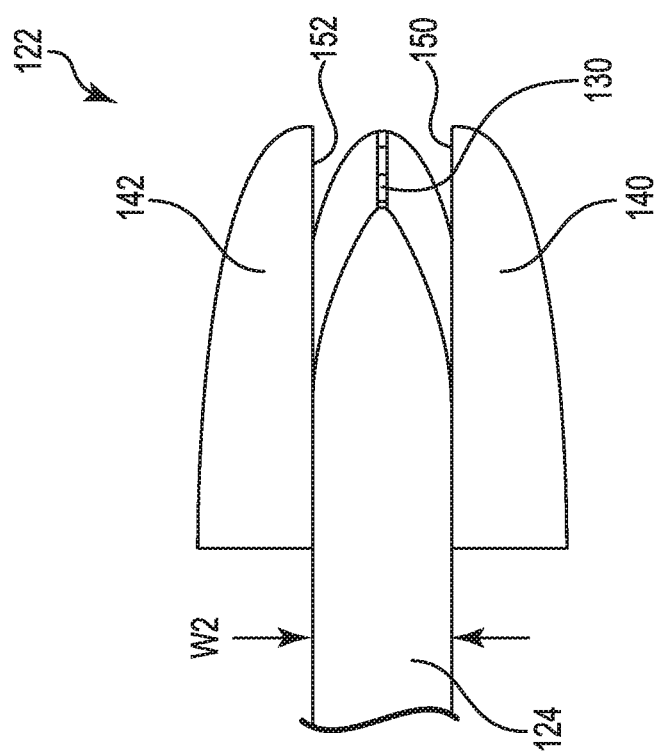

FIG. 6A is a bottom view and FIG. 6B is an end view of the pincher 122 of the tool 120 in the closed position.

The plunger 124 has been moved in a distal direction to push the first plunger edge 150 away from the second plunger edge 152, thereby increasing the distance between the plunger edges 150, 152. As illustrated in FIG. 6A, the first plunger edge 150 has been displaced away from the second plunger edge 152 by a distance that is substantially equal to the second width W2 of the plunger 124. The second width W2 of the plunger 124 has been pushed between the plunger edges 150, 152 of the jaws 140, 142. The second width W2 of the plunger 124 is larger than the gap distance G (FIG. 5A), which results in the plunger 124 spreading the plunger edges 150, 152 apart and closing the pincher 122.

Note that as illustrated in FIG. 6B, a portion of the cross-sectional profile of the plunger 124 is wider than it is tall (or in other words, the cross-sectional profile of the plunger at that location is not circular). Circular cross-sectional profiles are acceptable for the plunger 124. Non-circular cross-sectional profiles are acceptable for the plunger 124.

Aspects of the disclosed linearly tapered plunger being tapered between the first width and the second width of the plunger provide the advantageous technical effect of reversibly closing and opening the pincher as the plunger smoothly interacts with edges of the pincher.

Aspects of the disclosed straight linear edge of the plunger provide the advantageous technical effect of reversibly closing and opening the pincher as the plunger slides relative to and interacts with edges of the pincher.

With regard to the pinchers, aspects of the disclosed straight linear edge of the plunger edge portion of the pincher provide the advantageous technical effect of allowing the plunger to smoothly and continuously slide relative to these edges of the pincher.

The plunger is movable relative to the handle to provide the advantageous technical effect of allowing the surgeon to manipulate the device through a pushing action of the thumb, or one hand, for example.

In some aspects the plunger is located "under" the handle to provide the advantageous technical effect of locating the plunger on a side of the handle opposite from the free edges of the first jaw and the second jaw to allow the surgeon a better line of sight when using the device.

In some aspects the pincher is C-shaped in lateral cross-section to provide the advantageous technical effect of engaging the implantable cylinder in a manner that allows the cylinder and the pincher to slide into the opening of the dilated corpora.

Figure 7:
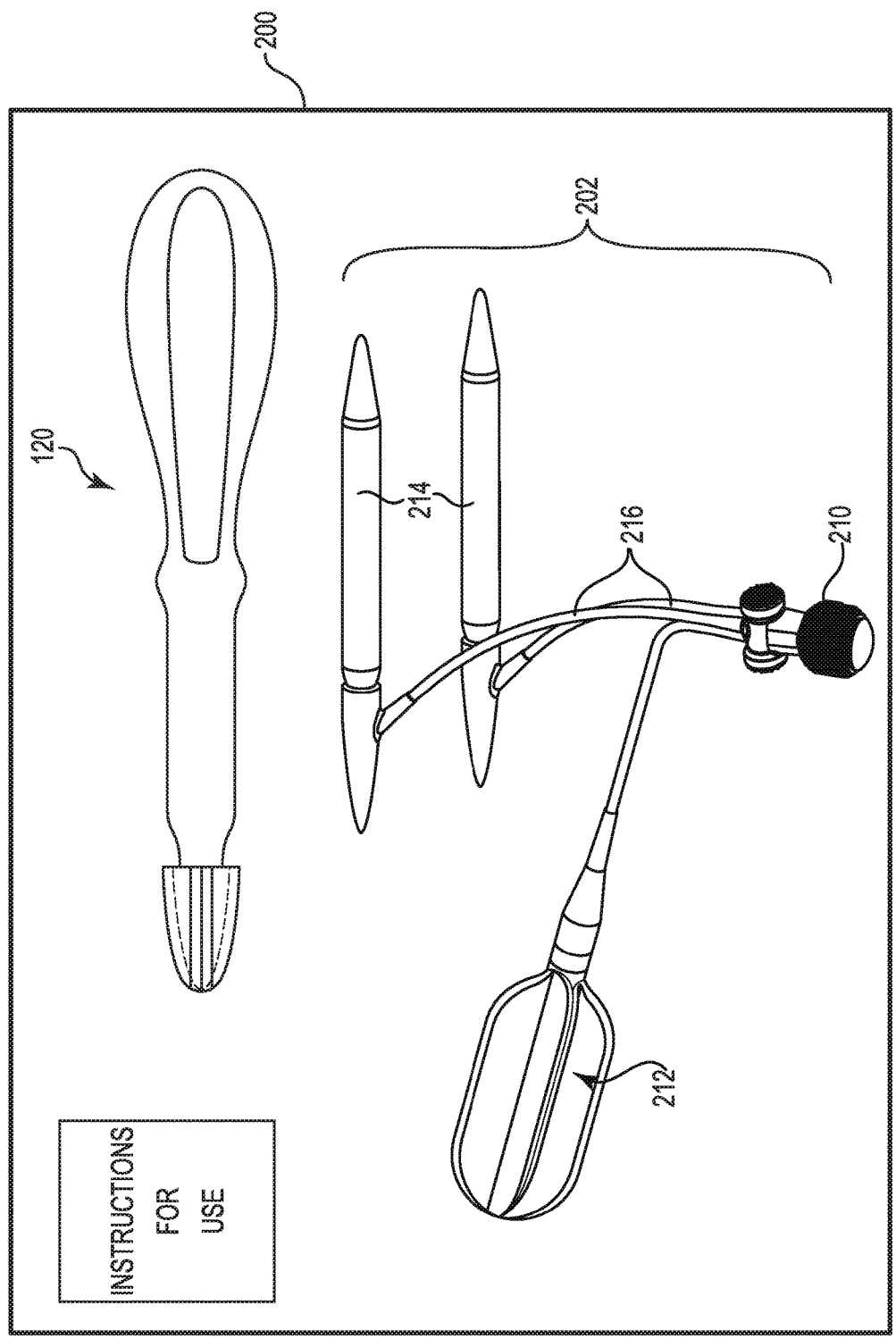
FIG. 7 is a schematic view of a kit of parts including the tool illustrated in FIG. 3A.

FIG. 7 is a schematic view of a kit of parts 200. The kit of parts includes the tool 120, an implantable penile prosthetic system 202, and instructions for use of the tool 100. The implantable penile prosthetic system 202 includes a pump 210 connectable between a reservoir 212 and two inflatable penile prosthetic cylinders 214. The implantable penile prosthetic system 202 is shown in an assembled state for simplicity of discussion with the cylinders 214 connected to the pump 210 by tubing 216. Typically, the cylinders 214 are connected to the pump 210 after implantation. The pump 210 operates to move liquid from the reservoir 212 into the inflatable cylinders 214. The inflated cylinders 214, when implanted, provide the penis with an erection.

Figure 8:
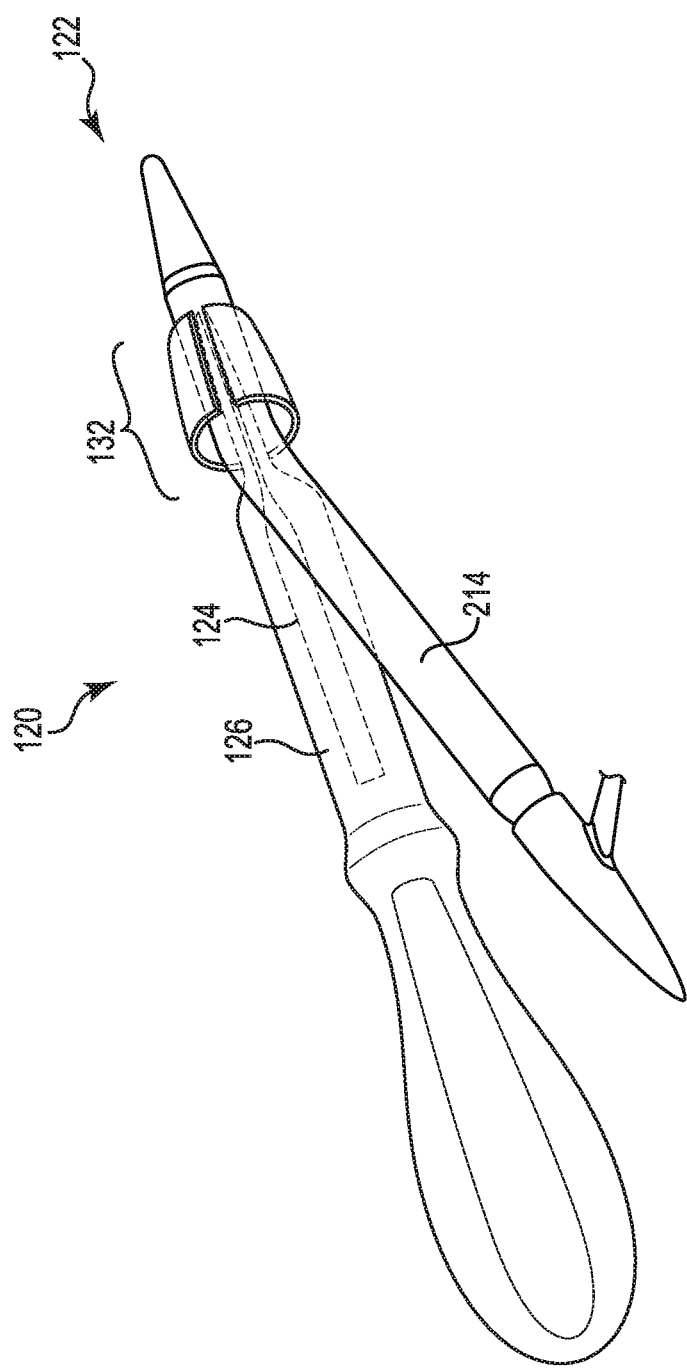
FIG. 8 is a perspective view of an inflatable penile cylinder captured by the pincher of the tool.

FIG. 8 is a perspective view of a cylinder 214 captured by the pincher 122. The pincher 122 has closed around the distal end portion of the cylinder 214 to allow the tool 120 to insert the cylinder 214 into a dilated corpora cavernosum. In some aspects the pincher 122 grasps the distal end of the cylinder, and in other aspects the pincher 122 grasps the cylinder proximal to the distal end to allow the distal end of the cylinder to "tunnel" forward into the dilated corpora.

One example of the use of the tool 120 includes the surgeon inserting the cylinder 214 within the pincher 122 and pushing the plunger 124 in the distal direction. Pushing the plunger 124 in the distal direction closes the pincher 122 onto the cylinder 214. Pushing the tool 120 and the cylinder 214 in the distal direction into the corpora cavernosum moves the cylinder 214 into the penis while at the same time maintaining the pinch force of the pincher 122 against the cylinder 214. When the surgeon determines that the cylinder 214 has been properly placed, the surgeon releases the forward (distal) force applied to the plunger 124 and withdraws the tool 120 from the penis. The pincher 122 releases its grasp from the cylinder 214 allowing the pincher 122 to slide along the cylinder 214.

Embodiments provide an improved tool for implanting a prosthetic cylinder of an implantable device useful for treating erectile dysfunction. The tool described in this application obviates the use of a Keith needle and does away with perforating the glans penis when implanting a prosthetic cylinder.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method of implanting a penile prosthetic, the method comprising:
    forming an incision in a penis and accessing a corpora cavernosum of the penis;
    dilating tissue in the corpora cavernosum and providing a dilated corpora cavernosum;
    using a tool, where the tool has a spine portion that is movably coupled to a handle, a plunger coupled to the handle, a first jaw movably coupled to a second jaw along the spine portion of the tool, where the first jaw has a first plunger edge that is spaced a gap distance away from a second plunger edge of the second jaw;
    moving the plunger to a location between the first plunger edge and the second plunger edge and grasping a penile prosthesis between the first jaw and the second jaw;
    inserting the first jaw and the second jaw and a portion of the penile prosthesis into the dilated corpora cavernosum;
    removing the plunger from the location between the first plunger edge and the second plunger edge and releasing the penile prosthesis from the first jaw and the second jaw; and
    removing the first jaw and the second jaw out the dilated corpora cavernosum and leaving the penile prosthesis in the dilated corpora cavernosum.

2. The method of claim 1, wherein the plunger is a tapered plunger having a first width at a distal end that is not greater than the gap distance and a second width that is larger than the first width, with the method comprising:
    moving the second width of the tapered plunger between the first plunger edge and the second plunger edge and grasping the penile prosthesis between the first jaw and the second jaw.

3. The method of claim 1, wherein the plunger is a tapered plunger having a first width at a distal end that is not greater than the gap distance and a second width that is larger than the first width, with the method comprising:
    displacing the second width of the tapered plunger from between the first plunger edge and the second plunger edge and releasing the penile prosthesis from the first jaw and the second jaw.

4. The method of claim 1, comprising inserting the first jaw and the second jaw and the portion of the penile prosthesis into the dilated corpora cavernosum while maintaining a pinch force of the tool against the penile prosthesis.

5. The method of claim 1, further comprising removing the first jaw and the second jaw out the dilated corpora cavernosum and sliding the first jaw and the second jaw along the penile prosthesis.

6. The method of claim 1, moving the plunger to a location between the first plunger edge and the second plunger edge comprises moving the plunger relative to the handle.

7. The method of claim 1, wherein a portion of the plunger is located inside of the handle, and the method further comprises moving the plunger within the handle.

8. The method of claim 1, wherein the tool has a bullet-shaped profile that tapers to a rounded distal end, and the method further comprises:
    inserting the rounded distal end of the tool into the dilated corpora cavernosum to a location within a glans penis.

9. The method of claim 1, comprising pushing a push button of the plunger and moving the plunger between the first plunger edge and the second plunger edge and grasping the penile prosthesis between the first jaw and the second jaw.

10. The method of claim 1, comprising moving the plunger between the first plunger edge and the second plunger edge and grasping an inflatable cylinder of the penile prosthesis between the first jaw and the second jaw.

11. A method of implanting a penile prosthetic, the method comprising:
    forming an incision in a penis and accessing a corpora cavernosum of the penis;
    dilating tissue in the corpora cavernosum and providing a dilated corpora cavernosum;
    using a tool, where the tool has a plunger, a first jaw movably coupled to a second jaw along a spine portion of the tool, where the first jaw has a first plunger edge that is spaced a gap distance away from a second plunger edge of the second jaw;
    moving the plunger in a first direction between the first plunger edge and the second plunger edge and grasping a penile prosthesis between the first jaw and the second jaw;
    inserting the first jaw and the second jaw and a portion of the penile prosthesis into the dilated corpora cavernosum;
    moving the plunger in a second direction opposite from the first direction between the first plunger edge and the second plunger edge and releasing the penile prosthesis from the first jaw and the second jaw; and
    removing the first jaw and the second jaw out the dilated corpora cavernosum and leaving the penile prosthesis in the dilated corpora cavernosum.

12. A method of implanting a penile prosthetic, the method comprising:
    forming an incision in a penis and accessing a corpora cavernosum of the penis;
    dilating tissue in the corpora cavernosum and providing a dilated corpora cavernosum;

using a tool, where the tool has a tapered plunger, a first jaw movably coupled to a second jaw along a spine portion of the tool, where the first jaw has a first plunger edge that is spaced a gap distance away from a second plunger edge of the second jaw;

moving the tapered plunger in a distal direction between the first plunger edge and the second plunger edge and grasping a penile prosthesis between the first jaw and the second jaw;

inserting the first jaw and the second jaw and a portion of the penile prosthesis into the dilated corpora cavernosum;

moving the tapered plunger in a proximal direction between the first plunger edge and the second plunger edge and releasing the penile prosthesis from the first jaw and the second jaw; and removing the first jaw and the second jaw out the dilated corpora cavernosum and leaving the penile prosthesis in the dilated corpora cavernosum.

* * * * *